United States Patent [19]

Laanio et al.

[11] 4,340,747

[45] Jul. 20, 1982

[54] ESTERS OF 1,2-DIPHENYL-CYCLOHEX-1-ENE-4-CARBOXYLIC-ACID

[75] Inventors: Verena Laanio, Arisdorf; Werner Föry, Basel; Rolf Schurter, Binningen, all of Switzerland

[73] Assignee: Ciba-Geigy Corporation, Ardsley, N.Y.

[21] Appl. No.: 151,034

[22] Filed: May 19, 1980

Related U.S. Application Data

[60] Division of Ser. No. 918,212, Jun. 22, 1978, Pat. No. 4,229,207, which is a continuation-in-part of Ser. No. 713,477, Aug. 11, 1976, abandoned.

[30] Foreign Application Priority Data

Aug. 15, 1975 [CH] Switzerland ........................ 1664/75
Aug. 15, 1975 [CH] Switzerland ........................ 1665/75
Aug. 15, 1975 [CH] Switzerland ........................ 1666/75

[51] Int. Cl.$^3$ .................... C07C 79/46; C07C 69/76
[52] U.S. Cl. .................................... 560/102; 560/21; 560/59
[58] Field of Search .................. 560/102, 21, 59; 71/106, 107, 76, 78

[56] References Cited

U.S. PATENT DOCUMENTS

3,546,343 12/1970 Payne, Jr. et al. .................... 71/106
3,639,454 2/1972 Richter ................................. 71/106
3,944,411 3/1976 Rohr .................................... 71/107
3,947,264 3/1976 Graham et al. ........................ 71/76
4,062,669 12/1977 Franz ..................................... 71/76

OTHER PUBLICATIONS

Valega et al., "Structure—Activity etc;" (1967) J. Econ. Ent. 60 pp. 341–347 (1967).
Monnin, "Dienophilic properties, etc;" (1958) CA 53 p. 10072c (1959).
Martirosyan et al., "Diene synthesis, etc;" (1971) CA 76, No. 3514a (1972).
Knoll, "Basic esters" (1958) CA 55, pp. 17544–17545 (1961).
Alder et al., "Arylated dienes: etc;" (1951) CA 45 pp. 4684–4686 (1951).
Gramenitskaya, "Growing activity, etc;" (1975) CA 83 No. 127364v (1975).

*Primary Examiner*—Glennon H. Hollrah
*Attorney, Agent, or Firm*—Frederick H. Rabin

[57] ABSTRACT

Esters of 1,2-diphenyl-cyclohex-1-ene-4-carboxylic-acid are effective plant growth regulating agents. They are useful for controlling wild oats in cereal cultures and for growth inhibition in different cultures, e.g. for the inhibition of suckers in tobacco plants.

11 Claims, No Drawings

ESTERS OF 1,2-DIPHENYL-CYCLOHEX-1-ENE-4-CARBOXYLIC-ACID

CROSS REFERENCE TO RELATED APPLICATION

This is a divisional of application Ser. No. 918,212 filed on June 22, 1978 now U.S. Pat. No. 4,229,207, which is a continuation-in-part of application Ser. No. 713,477, filed on Aug. 11, 1976, (now abandoned).

The invention relates to esters of 1,2-diphenyl-cyclohex-1-ene-4-carboxylic-acid with plant growth regulating activity, to compositions containing them and methods for inhibiting the growth of plants e.g. tobacco succers or controlling wild oats in cereal cultures with them.

The 1,2-diphenyl-cyclohex-1-ene-4-carboxylic-acid esters correspond to formula I

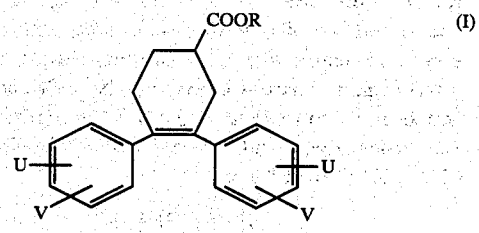

wherein

R is $C_1-C_{18}$ alkyl, optionally substituted by halogen, a $C_1-C_4$ alkoxy or $C_3-C_8$ cycloaliphatic radical or by phenyl or phenoxy, which in turn are optionally substituted by chlorine, bromine, $C_1-C_4$ alkyl or $C_1-C_4$ alkoxy.

$C_3-C_{18}$ alkenyl optionally substituted by chlorine, bromine or $C_1-C_4$ alkoxy, $C_3-C_6$ alkynyl, $C_3-C_{12}$ cycloalkyl optionally substituted by chlorine, bromine or methyl; phenyl or benzyl optionally substituted by chlorine, bromine, $C_1-C_4$ alkyl, $C_1-C_4$ alkoxy, nitro or trifluoromethyl, U and V are hydrogen, chlorine or bromine, $C_1-C_4$ alkyl, $C_1-C_4$ alkoxy, nitro, or trifluoromethyl.

The 1,2-diphenyl-cyclohex-1-ene-4-carboxylic-acid, which may also be termed 3,4-diphenyl-Δ3-tetrahydrobenzoic acid is known from Liebigs Ann. 570 201 (1950). No mention is made in the literature of a plant-influencing activity. Such activity becomes particularly evident in the present esters of this acid or in similar acids which are substituted in the phenyl ring according to this invention.

The following esters of 1,2-diphenyl-cyclohex-1-ene-4-carboxylic-acid were noticably active. The ones wherein U and V are hydrogen. Further those wherein R is $C_1$ to $C_7$ alkyl or $C_3$ to $C_7$ alkenyl optionally substituted by $C_1-C_4$ alkoxy. Exceptional activity showed the esters of 1,2-diphenyl-cyclohex-1-ene-4-carboxylic-acid wherein R is 2-bromoethyl, 2-fluoroethyl, 2,2,2-trichloroethyl, isopropyl, isobutyl, neopentyl and especially the methyl ester.

The compounds of formula I are prepared by reacting acrylonitrile, acrylic acid or a derivative thereof according to formula II $$CH_2=CH-COX \qquad (II)$$

wherein X is halogen, hydroxyl or OR, with either a diene of formula III

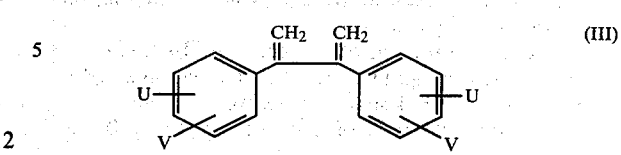

in a Diels-Alder reaction, or with a compound of the formula IIIa

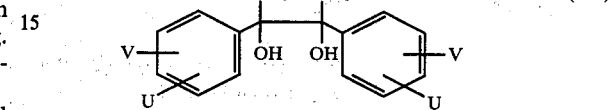

in a modified Diels-Alder reaction (Proc. Chem. Soc. 1963, 217), which is followed, if acrylic acid is used, if desired by an esterification with the appropriate alcohol R—OH or a reactive derivative thereof, or if acrylonitrile is used, initially by a saponification of the nitrile group to give the carboxyl group followed by optional esterification thereof. The substituents U and V are as defined for formula I.

The process of the invention is consequently a cyclisation reaction in the presence of a functional acid group, which in turn is either in the form of an acid or ester group, or, if desired, can be converted into such a group after the cyclisation is complete.

It will be readily understood that there are a number of ways of accomplishing this ester formation which is necessary before or after cyclisation. The following possibilities are cited as examples:

(a) reaction of —COOH with the halide, preferably chloride or bromide, R-halogen in the absence, but preferably in the presence, of a base;

(b) reaction of —COOH with the alcohol R—OH in the presence of acid catalysts (HCl, $H_2SO_4$, Lewis acids);

(c) transesterification of —COOR' (OR' is any alcoholic or phenolic group) with an excess of the desired alcohol R—OH, preferably also in the presence of an acid catalyst;

(d) reaction of a reactive acid derivative —COX with the alcohol R—OH or an alkali; salt thereof, wherein X represents a halide or another readily removable radical, such as benzene sulphate, tosylate, mesylate or the like.

Acid halides are customarily obtained by halogenating the carboxyl group with, for example, $SO_2Cl_2$, $COCl_2$, $(COCl)_2$, $PCl_5$, $PBr_5$, $SF_4$ and the like.

The conversion of a 1,2-diphenyl-cyclohexene-4-carboxylic acid into salts is carried out in conventional manner with a corresponding base defined in formula I.

The cyclisation process of this invention is carried out at normal pressure or elevated pressure in the temperature range between 80° and 200° C., preferably between 120° and 150° C., in solvents which are suitable for Diels-Alder reactions, such as hydrocarbons (benzene, toluene, xylenes) [cf. H. Wollweber "Diels-Alder-Reaktionen", Georg Thieme Verlag, Stuttgart, 1972]. The process, however, can also be carried out in the absence of a solvent.

When using compound IIIa, the addition of dehydrating agents (splitting off of 2 moles of water) is necessary to form compound III as intermediate. It is possible to use conventional agents, such as Al₂O₃, p-toluenesulphonic acid, KHSO₄, acetic anhydride/sodium acetate etc., for the dehydration.

The starting products of the formulae III and IIIa are partly known compounds are they can be obtained by methods which are known per se, for example:

"Grignard" reaction of the corresponding benzile derivatives

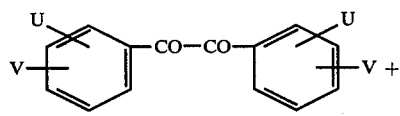

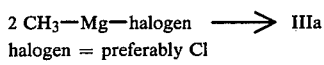

halogen = preferably Cl

[Bull. Soc. Chim France 43, 873 (1928)]

Dimerisation of the corresponding acetophenone derivative (a) electrochemically, (b) by irradiation (h·v), (c) in the presence of aluminium powder

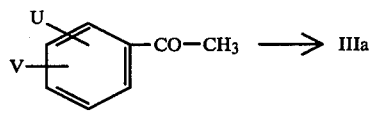

(a) [J. Am. Chem. Soc. 75, 5127 (1953)]
(b) [Tetrahedron 25, 4501 (1969)]
(c) [J. Org. Chem. 37, 2367 (1972)]

To prepare the optionally unsymetrical compounds of the formula III or IIIa in which the U's and V's have different meaning it is necessary to carry out a grignard reaction in one or two steps between diacetyl, CH₃—CO—CO—CH₃ and the different phenyl-magnesium-halogenides

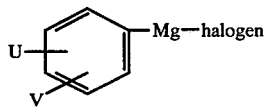

see J.Org.Chem. 28, 2154 (1963).

The following Examples illustrate the process of the present invention including the manufacture of the starting products. The parts are parts by weight. Further compounds of the formula I which were obtained by the described process are listed in the subsequent table.

EXAMPLE 1

(a) Manufacture of a starting product (1st method)

A mixture of 50 parts of 2,3-diphenyl-2,3-dihydroxybutane and 0.5 part of freshly dehydrated KHSO₄ is distilled for 50 minutes at 11 Torr and 200° C. bath temperature. The fraction which is collected within the boiling range of 150°–180° C./11 Torr yields 43.8 parts of crude 2,3-diphenyl-1,3-butadiene. The product is stirred direct with 21.5 parts of acrylic acid and 2 parts of hydroquinone under a nitrogen atmosphere for 3 hours at 130° to 140° C. The cooled reaction product is treated with diethyl ether and extracted with 1 normal NaOH. The aqueous phase is acidified with concentrated hydrochloric acid and extracted with diethyl ether. The organic phase is dried over Na₂SO₄ and concentrated in vacuo to yield 21 parts of 3,4-di-phenyl-Δ³-tetrahydrobenzoic acid with a melting point of 136°–140° C.

(b) (2nd method)

A mixture of 7.2 parts of 2,3-diphenyl-2,3-dihydroxybutane, 3.2 parts of acrylic acid, 0.1 part of p-toluenesulphonic acid and 0.3 part of hydroquinone is dissolved in 12 parts of acetone and the solution is kept for 25 minutes in a Carius tube. The solution is concentrated in vacuo and the oily residue is worked up as described in (a) above to yield 2.2 parts of 3,4-diphenyl-Δ³-tetrahydrobenzoic acid with a melting point of 136°–140° C.

EXAMPLE 2

A mixture of 57 parts of 3,4-diphenyl-Δ³-tetrahydrobenzoic acid and 5 parts of concentrated H₂SO₄ is kept for 18 hours in 500 parts by volume of methyl alcohol at reflux temperature. The solution is concentrated in vacuo and the oily residue is covered with a layer of ether and neutralised with 2 normal NaOH. The separated organic phase is dried over Na₂SO₄ and concentrated in vacuo to yield 57 parts of 3,4-diphenyl-Δ³-tetrahydrobenzoic acid methyl ester. Boiling point: 121°–125° C./0.001 Torr.

EXAMPLE 3

A mixture of 7.2 parts of 2,3-diphenyl-2,3-dihydroxybutane, 3.8 parts of acrylic acid methyl ester, 0.1 part of p-toluenesulphonic acid and 0.3 part of hydroquinone dissolved in 12 parts of acetic anhydride is kept in a Carius tube for 24 hours at 130°–140° C. The reaction product is distilled to yield 2.3 parts of 3,4-diphenyl-Δ³-tetrahydrobenzoic acid methyl ester. Boiling point: 121°–125° C./0.001 Torr.

EXAMPLE 4

(a) Manufacture of a starting product 27.8 parts of 3,4-diphenyl-Δ³-tetrahydrobenzoic acid are suspended in a mixture of 60 parts by volume of abs. chloroform and 0.8 part of dimethyl formamide. Then 15.5 parts of thionyl chloride are added dropwise at 0° C. in the course of 5 minutes. The mixture is stirred at 0° C. for 15 minutes at room temperature and stirred for 20 minutes at 40° C. The clear, yellow solution is concentrated in vacuo and dried in a high vacuum at 50° C. to yield 29 g of 3,4-diphenyl-Δ³-tetrahydrobenzoyl chloride. Boiling point: 160° C./0.005 Torr.

(b) A solution of 14.25 g (0.048 mole) of 3,4-diphenyl-Δ³-tetrahydrobenzoyl chloride in 80 ml of abs. ether is added dropwise at room temperature to a solution of 2.4 g (0.04 mole) of 1-propanol, 80 ml of abs. ether and 5 ml of pyridine. After 5 hours the reaction mixture is filtered through silica gel. The end product, 3,4-diphenyl-cyclohex-3-ene-1-carboxylic acid-n-propyl ester is eluted with petroleum ether/ether (2:1) and distilled in vacuo.

Yield: 7.2 g; b.p. (0.01 Torr) 150° C. (in a bulb tube). $n_D^{25}$ = 1.5665. The following compounds of the formula I are obtained in this manner or by one of the other methods indicated hereinabove:

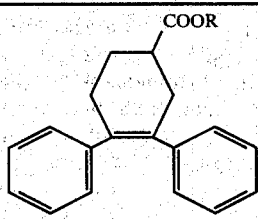

| Compound | R | Physical constant |
|---|---|---|
| 1 | CH$_3$ | b.p. 121–125° C./0.001 Torr |
| 2 | C$_2$H$_5$ | $n_D^{20}$ 1.5802 |
| 3 | n-C$_3$H$_7$ | $n_D^{25}$ 1.5665 |
| 4 | isoC$_3$H$_7$ | b.p. 165–170° C./0.01 Torr |
| 5 | n-C$_4$H$_9$ | $n_D^{25}$ 1.5617 |
| 6 | sec. C$_4$H$_9$ | $n_D^{25}$ 1.5560 |
| 7 | tert. C$_4$H$_9$ | $n_D^{25}$ 1.5430 |
| 8 | 3-C$_5$H$_{11}$ | $n_D^{20}$ 1.5560 |
| 9 | n-C$_8$H$_{17}$ | $n_D^{20}$ 1.5270 |
| 10 | n-C$_{12}$H$_{25}$ | $n_D^{20}$ 1.5179 |
| 11 | n-C$_{18}$H$_{37}$ | m.p. 45–47° C. |
| 12 | 2-bromoethyl | $n_D^{20}$ 1.5708 |
| 13 | 6-chlorohexyl(n) | $n_D^{20}$ 1.5625 |
| 14 | 3-nitrobutane-2-yl | $n_D^{25}$ 1.5585 |
| 15 | 2,2,2-trichloroethyl | $n_D^{20}$ 1.5800 |
| 16 | 2-cyanoethyl | m.p. 77–80° C. |
| 17 | 2-methoxyethyl | $n_D^{20}$ 1.5691 |
| 18 | 2-n-butoxyethyl | $n_D^{20}$ 1.5575 |
| 19 | 3-ethoxypropyl | $n_D^{20}$ 1.5600 |
| 20 | 2[2-butoxyethoxy]ethyl | $n_D^{25}$ 1.5485 |
| 21 | 2-allyloxyethyl | $n_D^{20}$ 1.5652 |
| 22 | 2-n-octylthioethyl | $n_D^{20}$ 1.5523 |
| 23 | 3-acetylpropyl | $n_D^{25}$ 1.5636 |
| 24 | —CH$_2$—CH$_2$—O—C(=O)—CH=CH$_2$ | $n_D^{20}$ 1.5640 |
| 25 | 2-fluoroethyl | m.p. 65–66° C. |
| 26 | 2-chloroethyl | m.p. 69–70° C. |
| 27 | 2-iodoethyl | $n_D^{25}$ 1.6072 |
| 28 | 3-chloropropyl(n) | $n_D^{25}$ 1.5753 |
| 29 | 3-bromopropyl(n) | $n_D^{25}$ 1.5845 |
| 30 | n-C$_5$H$_{11}$ | $n_D^{25}$ 1.5557 |
| 31 | isoC$_4$H$_9$ | $n_D^{25}$ 1.5592 |
| 32 | 1-ethoxycarbonyl-ethyl | $n_D^{20}$ 1.5570 |
| 33 | 3-N,N-dimethylamino-propyl | $n_D^{20}$ 1.5675 |
| 34 | (CH$_3$)$_3$N$^\oplus$—CH$_2$CH$_2$— Cl$^\ominus$ | m.p. 210–212° C. |
| 35 | cyclohexylmethyl | $n_D^{20}$ 1.5590 |
| 36 | cyclooctylmethyl | $n_D^{25}$ 1.5582 |
| 37 | cyclohexene-(3)-1-yl-methyl | $n_D^{25}$ 1.5697 |
| 38 | 3-phenylpropyl | $n_D^{20}$ 1.5873 |
| 39 | 2[4-methoxyphenyl]ethyl | m.p. 65–67° C. |
| 40 | 2-phenoxyethyl | $n_D^{20}$ 1.5850 |
| 41 | (tetrahydrofurfuryl) —CH$_2$— | $n_D^{25}$ 1.5610 |
| 42 | (tetrahydrofuran) —CH$_2$— | $n_D^{20}$ 1.5730 |
| 43 | (thiophene) —CH$_2$— | oil |
| 44 | (pyridyl) —CH$_2$CH$_2$— | $n_D^{20}$ 1.5892 |

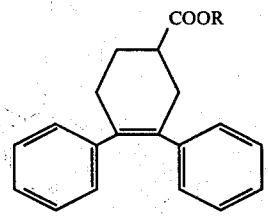

| Compound | R | Physical constant |
|---|---|---|
| 45 | morpholino—CH$_2$CH$_2$— | $n_D^{20}$ 1.5671 |
| 46 | 2-propenyl | $n_D^{20}$ 1.5762 |
| 47 | 4-pentenyl | $n_D^{20}$ 1.5652 |
| 48 | 3,7-dimethyl-octa-2,6-dien-1-yl | $n_D^{20}$ 1.5594 |
| 49 | 1-chloroprop-2-yl | $n_D^{25}$ 1.5671 |
| 50 | 1-bromoprop-2-yl | $n_D^{25}$ 1.5822 |
| 51 | 1,4-dibromobut-2-yl | oil |
| 52 | 2,3-dibromopropyl(n) | $n_D^{25}$ 1.5865 |
| 53 | 9-octadecenyl | $n_D^{20}$ 1.5290 |
| 54 | 2-propinyl | $n_D^{20}$ 1.5806 |
| 55 | 3-hexinyl | $n_D^{20}$ 1.5682 |
| 56 | 3-chloro-buten-(2)-yl | $n_D^{25}$ 1.5741 |
| 57 | 3-phenyl-propen-(2)-1-yl | $n_D^{20}$ 1.6065 |
| 58 | cyclopropyl | oil |
| 59 | cyclohexyl | $n_D^{20}$ 1.5639 |
| 60 | cyclooctyl | $n_D^{25}$ 1.5632 |
| 61 | cyclododecanyl | m.p. 95–100° C. |
| 62 | benzyl | $n_D^{20}$ 1.5935 |
| 63 | 4-chlorobenzyl | $n_D^{20}$ 1.5962 |
| 64 | 4-methoxybenzyl | $n_D^{20}$ 1.5910 |
| 65 | 4-methylbenzyl | $n_D^{20}$ 1.5930 |
| 66 | phenyl | $n_D^{20}$ 1.5881 |
| 67 | 3-bromophenyl | $n_D^{20}$ 1.6105 |
| 68 | 3,4-dichlorophenyl | $n_D^{20}$ 1.5982 |
| 69 | 4-chloro-2-methylphenyl | m.p. 118° C. |
| 70 | 4-methylthiophenyl | oil |
| 71 | 4-t-butylphenyl | $n_D^{20}$ 1.5782 |
| 72 | 3-nitrophenyl | $n_D^{25}$ 1.5940 |
| 73 | 4-sulphophenyl | oil |
| 74 | 3-cyanophenyl | $n_D^{25}$ 1.5910 |
| 75 | 3-trifluoromethylphenyl | $n_D^{25}$ 1.5598 |
| 76 | 3-N,N-dimethylamino-phenyl | $n_D^{25}$ 1.6000 |
| 77 | N-methylpiperidin-4-yl | oil |
| 78 | tetrahydrofuran-3-yl | m.p. 102–105° C. |
| 79 | 3-methoxycarbonyl-2-methyl-prop-2-en-1-yl | b.p. 210–215° C./0.001 Torr |
| 80 | 2-N,N-dimethylamino-ethyl | b.p. 165° C./0.01 Torr |
| 81 | 2-nitroethyl | oil |
| 82 | cyclopropylmethyl | oil |
| 83 | 1-cyclopropyl-eth-1-yl | $n_D^{25}$ 1.5643 |

The following compounds of the formula I are also obtained in the manner of one of the methods indicated above:

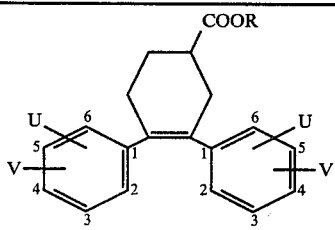

| Compound | U | V | R | Physical constant |
|---|---|---|---|---|
| 84 | 4-Cl | H | CH$_3$ | n$_D^{20}$ 1.5881 |
| 85 | 4-Cl | H | C$_2$H$_5$ | |
| 86 | 3-CH$_3$ | H | CH$_3$ | n$_D^{20}$ 1.5684 |
| 87 | 3-CH$_3$ | H | C$_2$H$_5$ | |
| 88 | 4-CH$_3$ | H | CH$_3$ | n$_D^{20}$ 1.5763 |
| 89 | 4-CH$_3$ | H | allyl | |
| 90 | 3-COOH | H | CH$_3$ | |
| 91 | 4-phenyl | H | CH$_3$ | m.p. 163–168° |
| 92 | 2-Cl | 4-Cl | isoC$_3$H$_7$ | |
| 93 | 4-Br | H | CH$_3$ | n$_D^{20}$ 1.6180 |
| 94 | 4-C$_2$H$_5$ | H | CH$_3$ | |
| 95 | 2-Cl | 3-Cl | C$_2$H$_5$ | |
| 96 | 3-Br | H | CH$_3$ | n$_D^{20}$ 1.6085 |
| 97 | 3-CF$_3$ | H | CH$_3$ | |
| 98 | 4-SO$_3$H | H | C$_2$H$_5$ | |
| 99 | 4-CN | H | CH$_3$ | oil |
| 100 | 4-N(CH$_3$)$_2$ | H | CH$_3$ | |
| 101 | 3-NO$_2$ | H | CH$_3$ | |
| 102 | 3-CH$_3$O | H | CH$_3$ | |
| 103 | 3-CH$_3$O | 5-CH$_3$O | CH$_3$ | oil |

The active substances of the present invention of the formula I, and the corresponding compositions which contain them, intervene in the physiological processes of plant development and can be used for various purposes in connection with the increase in yield, ease of harvesting and labour-saving in measures taken on cultivated plants. The various effects of these active substances depend substantially on the time of application (from the ripening stage of the plant) and on the concentrations employed. However, these effects are in turn different depending on the species of plant.

Compound structures of 4-phenyl-cyclohex-(3 or 4)-ene-1-carboxylates are disclosed within a substantial group of compounds in general form in German Offenlegungsschrift No. 1,900,658. Anti-fertility properties are ascribed to such compounds, which appear to make them suitable for rodent control. No particulars are given on effects on plants. That compounds of the formula I of the present invention act on plants is therefore completely surprising.

The active substances of this invention of the formula I, and the compositions which contain them, influence the plant growth. The supporting tissues of the stems of treated plants are strengthened. The formation of undesired suckers in various plant species is diminished, for instance the vegetative growth of vines is inhibited. Further the vegetative growth of soya bean and other leguminous plants is reduced and the generative growth promoted, whereby a direct increase in the yield is achieved.

Special mention is also to be made of the possibility of inhibiting the growth of suckers in tobacco plants with the active substances of the present invention, when the leading shoot has been cut off shortly before flowering in order to bring about the desired increase in growth of the leaves.

The principal kind of plant regulation, however, resides in the special property of the compounds of the formula I to effect in specific weeds a growth inhibition so pronounced that is approximates to a herbicidal action and the compounds can be used in practice for this purpose. When applied to a large number of monocotyledonous and dicotyledonous weeds (Setaria, Alopecurus, Sinapis, Galium etc.), the compounds effect a stunted growth. From the point of view of maintaining cultivated land, this effect provides a particularly advantageous weed control to the extent that, independently of the growth of useful plants, a uniform, low plant cover is retained, which counteracts soil erosion by wind or water. The marked selective activity of the compounds of the formula I, which either has no effect on the important major crops, such as sugar beet, wheat, barely, rye and others, or even—as in types of cereals—increases the breaking strength of the plant through slight growth reduction, results in an economically very interesting method of protecting cultivations of plants from the spread of weeds. A particularly advantageous feature of the compounds of the formula I is the pronounced herbicidal-like growth inhibition of wild oats (Avena fatua), which are among the most important grass-like weeds in crops of useful plants, above all in cereals. Experience has shown wild oats to be among the most difficult weeds to control. They are controlled only imperfectly by a few herbicides, but not at all by the majority of commercially available herbicides.

The invention therefore provides simultaneously a method of controlling weeds in crops of useful plants by applying compounds of the formula I, which cause stunted growth or compositions which contain them.

Such a method of inhibiting plant growth does not bring about any change in the sense of a mutation in the life cycle of the plant which is determined by genetic characteristics.

The maintenance of pure grass cultivations, such as those in public parks and gardens, in urban areas, industrial sites, or along main roads, railway embankments or the embankments of water bodies, has to be considered in connection with the reduction in growth of grasses. In all such cases it is normally necessary to cut the turf or grass periodically. This operation is not only time-consuming, complicated and expensive in respect of labour and machinery, but involves the personnel concerned and road users in considerable hazard in the traffic sector.

For this reason there is therefore an urgent need in areas with extensive traffic networks on the one hand to maintain and care for the grassy covering necessary for strengthening road shoulders and embankments on traffic routes, and on the other hand to keep it at reasonable height by simple means during the entire vegetation period. This need is fulfilled by a very advantageous manner by applying the compounds of the formula I.

The active substances of the formula I can be applied to the surface to be treated simultaneously or successively with further active substances. These active substances can be both fertilisers, trace element agents or other preparations which influence plant growth. However, they can also be selective herbicides, insecticides, fungicides, bactericides, nematicides, molluscicides or mixtures of these preparations, if appropriate together with additional carriers or further additives which assist application.

Suitable carriers or additives may be solid or liquid and correspond to the substances conventionally used in the art of formulation, for example: natural and regenerated substances, solvents, dispersing agents, wetting agents, stickers, thickeners, binders or fertilizers.

For application, the compounds of formula I can be in the following application forms.

Solid preparations:
dusts, tracking agents, granulates (coated granulates, impregnated granulates and homogranulates);

Liquid preparations:
(a) water-dispersible active substance concentrates: wettable powders, pastes or emulsions;
(b) solutions.

To these mixtures can also be added additives which stabilise the active substance and/or non-ionic, anionic and cationic substances, which for example improve the adhesion of the active ingredients on plants or parts of plants (stickers) and/or ensure a better wettability (wetting agents) and dispersibility (dispersing agents). Examples of suitable stickers are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation product of urea and formaldehyde, and also latex products.

Water-dispersible concentrates of the active substance, i.e. wettable powders, pastes and emulsifiable concentrates, are compositions which can be diluted with water to any desired concentration. They consist of active substance, carrier, optionally additives which stabilise the active substance, surface-active substances and anti-foam agents and, optionally, solvents.

The content of active substance in the above described compositions is between 0.1 and 95%, preferably between 1 and 80%. Application forms can be diluted to as low a content of active substance as 0.001%. As a rule the rates of application are from 0.1 to 10 kg of active substance per hectare, preferably from 0.25 to 5 kg per hectare.

The active substances of formula I can be formulated for example in the following way:

DUSTS

The following substances are used for the preparation of (a) a 5% (b) a 2% dust:

| | |
|---|---|
| (a) | 5 parts of active substance |
| | 95 parts of talcum |
| (b) | 2 parts of active substance |
| | 1 part of highly dispersed silicic acid |
| | 97 parts of talcum |

The active ingredients are mixed and ground with the carriers.

GRANULATE

The following substances are used to obtain a 5% granulate:

5 parts of active substance
0.25 parts of epichlorohydrin
0.25 parts of cetyl polyglycol ether 3.50 parts of polyethylene glycol
91 parts of kaolin (particle size 0.3–0.8 mm)

The active substance is mixed with epichlorohydrin and dissolved in 6 parts of acetone, then the polyethylene glycol and cetyl polyglycol ether are added. The resultant solution is sprayed onto kaolin and the acetone is subsequently evaporated in vacuo.

WETTABLE POWDER

The following ingredients are used to prepare a 25% wettable powder.

25 parts of active substance,
4.5 parts of calcium lignin sulphonate,
1.9 parts of Champagne chalk/hydroxyethyl cellulose mixture (1:1),
1.5 parts of sodium dibutyl naphthalenesulphonate,
19.5 parts of silicic acid,
19.5 parts of Champagne chalk,
28.1 parts of kaolin;

The active substances are intimately mixed in suitable mixers with the additives, and the mixture is then milled in appropriate mills and rollers. Wettable powders are obtained which can be diluted with water to give suspensions of any desired concentration.

EMULSIFIABLE CONCENTRATES

The following substances are used to produce a 25% emulsifiable concentrate:

250 parts of active substance
150 parts of a condensation product of 1 mole of tributylphenol and 10 moles of ethylene oxide as wetting agent. The preparation is bulked to a volume of 1000 ml with xylene.

By diluting such concentrates with water it is possible to obtain emulsions of any desired concentration which are suitable for application to plants to inhibit their growth. To illustrate the plant growth influencing properties of the compounds of the formula I, the herbicidal/growth-inhibiting activity was determined by means of the following tests.

TEST A

Herbicidal post-emergence application in the greenhouse

Plant seeds were sown into pots filled with sterilized earth, so that 8 to 20 plants could develop. Then they were left to emerge and when the young plants had 2 to 3 true leaves after 10 to 12 days, they were sprayed with a testing solution containing the active substance. The concentration was so chosen as to correspond to an application rate in a field of 8, 4, 2, 1 and ½ kg of active substance per hectare. The plants were then left to develop in the green-house for three weeks under optimal conditions of light, temperature and humidity and regular watering. Then the test was evaluated and the state of the plants assessed according to the following scale 9 plant develops normally, like untreated control plants
8–5 light to medium stages of damage
5–2 severe stages of damage
1 plant died
— plant at corresponding concentration not tested.

The results are summarized in the table below.

| compound No. application | 1 | | | | 15 | | | | 2 | | | | 25 | | | | 26 | | | |
|---|---|---|---|---|---|---|---|---|---|---|---|---|---|---|---|---|---|---|---|---|
| rate kg/ha | 8 | 4 | 2 | 1 | 8 | 4 | 2 | 1 | 4 | 2 | 1 | ½ | 8 | 4 | 2 | 1 | 8 | 4 | 2 | 1 |
| plant | | | | | | | | | | | | | | | | | | | | |
| barley | 7 | 8 | 9 | 9 | 5 | 6 | 7 | 9 | 4 | 6 | 7 | 8 | 7 | 8 | 9 | 9 | 9 | 9 | 9 | 9 |
| wheat | 8 | 9 | 9 | 9 | 9 | 9 | 9 | 9 | 4 | 6 | 7 | 8 | 7 | 9 | 9 | 9 | 9 | 9 | 9 | 9 |
| maize | 2 | 4 | 6 | 7 | 6 | 7 | 9 | 9 | 5 | 8 | 9 | 9 | 4 | 8 | 9 | 9 | 6 | 7 | 9 | 9 |
| sorgho | 9 | 9 | 9 | 9 | 7 | 8 | 9 | 9 | 3 | 7 | 8 | 9 | 9 | 9 | 9 | 9 | 8 | 9 | 9 | 9 |
| rice | 9 | 9 | 9 | 9 | 8 | 9 | 9 | 9 | 9 | 9 | 9 | 9 | 8 | 9 | 9 | 9 | 9 | 9 | 9 | 9 |
| soya | 3 | 3 | 4 | 4 | 4 | 4 | 4 | 6 | 3 | 3 | 3 | 4 | 4 | 5 | 6 | 6 | 4 | 4 | 4 | 6 |
| cotton | 7 | 7 | 7 | 7 | 6 | 6 | 7 | 7 | 8 | 8 | 8 | 9 | 5 | 5 | 6 | 6 | 3 | 4 | 4 | 4 |
| Avena fatua | 4 | 4 | 4 | 4 | 4 | 4 | 5 | 6 | 3 | 3 | 3 | 4 | 3 | 3 | 4 | 4 | 4 | 4 | 4 | 4 |
| Lolium perenne | 8 | 9 | 9 | 9 | 9 | 9 | 9 | 9 | 6 | 6 | 7 | 9 | 9 | 9 | 9 | 9 | 8 | 9 | 9 | 9 |
| Alopecurus myosuroides | 6 | 7 | 8 | 9 | 5 | 7 | 7 | 7 | 3 | 4 | 4 | 6 | 5 | 6 | 7 | 8 | 6 | 7 | 8 | 9 |
| Cyperus esculentus | 7 | — | — | 7 | 9 | — | 9 | — | 7 | — | 9 | — | 8 | — | 9 | — | 5 | — | 7 | — |
| Rottboellia exaltata | 7 | 9 | 9 | 9 | 7 | 9 | 9 | 9 | 8 | 9 | 9 | 9 | 7 | 9 | 9 | 9 | 7 | 8 | 8 | 9 |
| Digitaria sanguinalis | 7 | 8 | 9 | 9 | 8 | 9 | 9 | 9 | 6 | 6 | 8 | 9 | 7 | 9 | 9 | 9 | 6 | 9 | 9 | 9 |
| Setaria italica | 8 | 9 | 9 | 9 | 7 | 8 | 9 | 9 | 7 | 7 | 8 | 9 | 9 | 9 | 9 | 9 | 7 | 9 | 9 | 9 |
| Echinochloa crus galli | 8 | 9 | 9 | 9 | 8 | 9 | 9 | 9 | 6 | 7 | 8 | 9 | 8 | 9 | 9 | 9 | 8 | 9 | 9 | 9 |
| Beta vulgaris | 7 | 8 | 9 | 9 | 8 | 9 | 9 | 9 | 9 | 9 | 9 | 9 | 9 | 9 | 9 | 9 | 9 | 9 | 9 | 9 |
| Sesbania exaltata | 7 | 7 | 9 | 9 | 7 | 8 | 9 | 9 | 8 | 9 | 9 | 9 | 5 | 8 | 8 | 8 | 7 | 7 | 8 | 9 |
| Amaranthus retroflexus | 6 | 7 | 9 | 9 | 6 | 7 | 7 | 7 | 7 | 7 | 9 | 9 | 5 | 6 | 8 | 8 | 5 | 7 | 7 | 9 |
| Sinapis alba | 3 | 4 | 4 | 4 | 6 | 6 | 6 | 6 | 3 | 4 | 6 | 6 | 4 | 6 | 6 | 6 | 3 | 4 | 4 | 5 |
| Ipomoea purpurea | 4 | 4 | 4 | 4 | 4 | 5 | 7 | 7 | 4 | 5 | 7 | 8 | 5 | 7 | 7 | 9 | 3 | 6 | 7 | 8 |
| Galium aparine | 6 | 6 | 6 | 6 | 5 | 6 | 7 | 7 | 5 | 6 | 6 | 7 | 7 | 7 | 7 | 7 | 7 | 7 | 7 | 7 |
| Pastinaca sativa | 7 | 9 | 9 | 9 | 9 | 9 | 9 | 9 | 9 | 9 | 9 | 9 | 8 | 9 | 9 | 9 | 7 | 9 | 9 | 9 |
| Matricaria chamomille | 7 | 8 | 9 | 9 | 8 | 9 | 9 | 9 | 8 | 8 | 9 | 9 | 8 | 9 | 9 | 9 | 9 | 9 | 9 | 9 |
| Sida spinosa | 6 | 6 | 7 | 9 | 7 | 7 | 9 | 9 | 7 | 7 | 8 | 8 | 3 | 6 | 9 | 9 | 4 | 6 | 6 | 6 |
| Rumex sp. | 5 | 5 | 6 | 6 | 4 | 6 | 6 | 9 | 3 | 3 | 3 | 4 | 5 | 6 | 6 | 6 | 4 | 4 | 5 | 5 |

| compound No. application | 29 | | | | 3 | | | | 31 | | | | 46 | | | | 5 | | | | 8 | | | | 83 | | | |
|---|---|---|---|---|---|---|---|---|---|---|---|---|---|---|---|---|---|---|---|---|---|---|---|---|---|---|---|---|
| rate kg/ha | 8 | 4 | 2 | 1 | 8 | 4 | 2 | 1 | 8 | 4 | 2 | 1 | 8 | 4 | 2 | 1 | 8 | 4 | 2 | 1 | 8 | 4 | 2 | 1 | 8 | 4 | 2 | 1 |
| plant | | | | | | | | | | | | | | | | | | | | | | | | | | | | |
| barley | 9 | 9 | 9 | 9 | 7 | 8 | 8 | 9 | 9 | 9 | 9 | 9 | 7 | 7 | 9 | 9 | 7 | 8 | 9 | 9 | 9 | 9 | 9 | 9 | 9 | 9 | 9 | 9 |
| wheat | 9 | 9 | 9 | 9 | 7 | 9 | 9 | 9 | 7 | 9 | 9 | 9 | 8 | 9 | 9 | 9 | 9 | 9 | 9 | 9 | 9 | 9 | 9 | 9 | 9 | 9 | 9 | 9 |
| maize | 6 | 7 | 9 | 9 | 6 | 7 | 9 | 9 | 5 | 7 | 9 | 9 | 6 | 7 | 7 | 9 | 6 | 7 | 8 | 8 | 7 | 7 | 9 | 9 | 7 | 8 | 9 | 9 |
| sorgho | 9 | 9 | 9 | 9 | 7 | 9 | 9 | 9 | 9 | 9 | 9 | 9 | 7 | 8 | 9 | 9 | 9 | 9 | 9 | 9 | 9 | 9 | 9 | 9 | 9 | 9 | 9 | 9 |
| rice | 9 | 9 | 9 | 9 | 8 | 9 | 9 | 9 | 9 | 9 | 9 | 9 | 7 | 7 | 9 | 9 | 9 | 9 | 9 | 9 | 9 | 9 | 9 | 9 | 9 | 9 | 9 | 9 |
| soya | 5 | 5 | 7 | 8 | 4 | 5 | 6 | 6 | 4 | 4 | 4 | 4 | 4 | 4 | 4 | 5 | 5 | 6 | 6 | 6 | 4 | 4 | 7 | 7 | 7 | 7 | 7 | 8 |
| cotton | 3 | 3 | 4 | 5 | 4 | 5 | 5 | 5 | 4 | 4 | 4 | 7 | 6 | 7 | 7 | 8 | 4 | 4 | 6 | 6 | 6 | 7 | 7 | 7 | 4 | 6 | 6 | 7 |
| Avena fatua | 3 | 3 | 3 | 6 | 3 | 3 | 4 | 5 | 3 | 3 | 3 | 6 | 3 | 3 | 4 | 5 | 3 | 4 | 4 | 5 | 3 | 3 | 4 | 4 | 4 | 4 | 4 | 4 |
| Lolium perenne | 9 | 9 | 9 | 9 | 7 | 8 | 9 | 9 | 8 | 9 | 9 | 9 | 9 | 9 | 9 | 9 | 7 | 9 | 9 | 9 | 8 | 9 | 9 | 9 | 9 | 9 | 9 | 9 |
| Alopecurus myosuroides | 6 | 6 | 7 | 8 | 4 | 6 | 6 | 8 | 4 | 6 | 6 | 7 | 3 | 3 | 5 | 6 | 4 | 5 | 5 | 9 | 8 | 9 | 9 | 9 | 4 | 6 | 6 | 8 |
| Cyperus esculentus | 8 | — | 8 | — | 7 | — | 9 | 9 | 7 | — | 8 | — | — | — | — | — | 8 | — | 8 | — | 9 | — | 9 | — | 8 | — | 9 | — |
| Rottboellia exaltata | 9 | 9 | 9 | 9 | 8 | 8 | 9 | 9 | 8 | 8 | 9 | 9 | 6 | 8 | 8 | 9 | 8 | 9 | 9 | 9 | 7 | 8 | 8 | 9 | 8 | 9 | 9 | 9 |
| Digitaria sanguinalis | 4 | 8 | 8 | 9 | 6 | 6 | 7 | 7 | 9 | 9 | 9 | 9 | 9 | 9 | 9 | 9 | 8 | 9 | 9 | 9 | 7 | 7 | 9 | 9 | | | | |
| Setaria italica | 4 | 7 | 7 | 9 | 5 | 7 | 4 | 4 | 6 | 7 | 7 | 8 | 8 | 9 | 9 | 9 | 8 | 9 | 9 | 9 | 7 | 8 | 9 | 9 | 4 | 4 | 7 | 7 |
| Echinochloa crus galli | 9 | 9 | 9 | 9 | 6 | 7 | 9 | 9 | 9 | 9 | 9 | 9 | 7 | 8 | 9 | 9 | 9 | 9 | 9 | 9 | 9 | 9 | 9 | 9 | 9 | 9 | 9 | 9 |
| Beta vulgaris | 9 | 9 | 9 | 9 | 6 | 9 | 9 | 9 | 9 | 9 | 9 | 9 | 8 | 8 | 9 | 9 | 9 | 9 | 9 | 8 | 9 | 9 | 9 | 9 | 9 | 9 | 9 | 9 |
| Sesbania exaltata | 7 | 8 | 9 | 9 | 4 | 7 | 9 | 9 | 7 | 8 | 9 | 9 | 7 | 8 | 9 | 9 | 6 | 7 | 8 | 9 | 9 | 9 | 9 | 7 | 8 | 9 | 9 | 9 |
| Amaranthus retroflexus | 7 | 7 | 8 | 9 | 7 | 8 | 9 | 9 | 7 | 7 | 8 | 9 | 6 | 6 | 7 | 7 | 6 | 6 | 7 | 8 | 6 | 7 | 8 | 9 | 8 | 8 | 9 | 9 |
| Sinapis alba | 5 | 5 | 7 | 9 | 3 | 4 | 8 | 9 | 3 | 3 | 3 | 4 | 3 | 3 | 4 | 6 | 4 | 4 | 4 | 4 | 5 | 5 | 5 | 5 | 5 | 5 | 5 | 6 |
| Ipomoea purpurea | 4 | 7 | 7 | 7 | 4 | 5 | 6 | 7 | 4 | 6 | 7 | 7 | 4 | 4 | 6 | 6 | 4 | 7 | 8 | 8 | 6 | 6 | 7 | 7 | 6 | 7 | 8 | 9 |
| Galium aparine | 7 | 7 | 9 | 9 | 6 | 6 | 6 | 6 | 8 | 8 | 8 | 8 | 5 | 6 | 6 | 6 | 7 | 7 | 7 | 5 | 5 | 5 | 5 | 8 | 8 | 9 | 9 | |
| Pastinaca sativa | 9 | 9 | 9 | 9 | 6 | 8 | 9 | 9 | 9 | 9 | 9 | 9 | 8 | 9 | 9 | 9 | 9 | 9 | 9 | 9 | 9 | 9 | 9 | 9 | 9 | 9 | 9 | 9 |
| Matricaria chamomille | 9 | 9 | 9 | 9 | 6 | 7 | 9 | 9 | 7 | 9 | 9 | 9 | 9 | 9 | 9 | 9 | 9 | 9 | 9 | 9 | 9 | 9 | 9 | 9 | 9 | 9 | 9 | 9 |
| Sida spinosa | 4 | 4 | 6 | 6 | 4 | 4 | 9 | 9 | 6 | 6 | 6 | 9 | 7 | 7 | 8 | 8 | 4 | 4 | 7 | 4 | 7 | 8 | 9 | 9 | 6 | 9 | 9 | 9 |
| Rumex sp. | 4 | 6 | 6 | 6 | 3 | 4 | 9 | 9 | 4 | 5 | 5 | 5 | 3 | 4 | 5 | 5 | 4 | 4 | 4 | 4 | 5 | 5 | 6 | 6 | 6 | 6 |

These compounds do not show excellent herbicidal activity in this test. Monocotyledonous plants are hardly damaged with the exception of Avena fatua. The activity is better towards some of the dicotyledonous plants. The possibility of controlling Avena fatua (wild oats) in cultures of cereal, barley wheat, sorgho or rice, is given. In order to investigate this, a field test was undertaken.

SMALL-FIELD TEST

A field in northeren Switzerland was divided into several small lots. These lots were then seeded with the following cultures.
- wheat of the variety "Probus"
- hard wheat
- barley of the variety "Nymphe"
- oats of the variety "Flämingskrone"

In between the culture plants the were seeded rows with the weeds Bromus tectorum, Alopecurus myosuroides, Lolium perenne and Avena fatua.

Four weeks, after the seeds have emerged and the young plants show 3 to 6 true leaves, the lots were sprayed with emulsions of the substance to be tested in concentrations of 4, 2, 1 and ½ kg/ha. Some of the lots were left untreated to serve as control. The test was evaluated after six weeks and the state of the plants assessed according to the above given scale. The results are summarized in the table below.

| compound application | No. 1 | | | | Destun ® | | | |
|---|---|---|---|---|---|---|---|---|
| rate kg/ha | 4 | 2 | 1 | ½ | 4 | 2 | 1 | ½ |
| plant | | | | | | | | |
| wheat "Probus" | 6 | 6 | 9 | 9 | 2 | 8 | 9 | 9 |
| hard wheat | 5 | 6 | 9 | 9 | 6 | 7 | 7 | 9 |
| barley "Nymphe" | 5 | 7 | 9 | 9 | 7 | 8 | 9 | 9 |
| oats "Flamingskrone" | 2 | 2 | 2 | 3 | 2 | 8 | 9 | 9 |
| Bromus tectorum | 9 | 9 | 9 | 9 | 2 | 3 | 8 | 9 |
| Alopecurus myosuroides | 9 | 9 | 9 | 9 | 9 | 9 | 9 | 9 |
| Lolium perenne | 9 | 9 | 9 | 9 | 4 | 5 | 8 | 9 |
| Avena fatua | 1 | 2 | 2 | 3 | 8 | 9 | 9 | 9 |

The compound "Destun ®" [1,1,1-trifluoro-N-(4-phenylsulfonyl-o-tolyl)-methane sulfamide] was not chosen for comparison because of structural likeness but because we expected it to show a similar activity.

FURTHER FIELD TESTS

Further tests were than conducted in different countries where because of climatic and topographic conditions, Avena fatua has become the problem weed in cereal. Because of its morphological likeness with the culture, this weed is difficult to control. The fields chosen for tests, were divided after emergence of the wheat (culture) into big lots of 100 m². These lots were then treated with emulsions of active substance until amounts of 4, 2, 1 and ½ kg/ha were applied. The part of the field that was not treated served as control. The test was evaluated (as above) after six weeks. The results are summarized in the table below.

| compound application | 1 | | | | Destun ® | | | |
|---|---|---|---|---|---|---|---|---|
| rate in kg/ha | 4 | 2 | 1 | ½ | 4 | 2 | 1 | ½ |
| country: Switzerland | | | | | | | | |
| wheat | 8 | 8 | 9 | 9 | 2 | 8 | 9 | 9 |

| compound application | 1 | | | | Destun ® | | | |
|---|---|---|---|---|---|---|---|---|
| rate in kg/ha | 4 | 2 | 1 | ½ | 4 | 2 | 1 | ½ |
| Avena fatua country: France | 1 | 2 | 2 | 3 | 8 | 9 | 9 | 9 |
| wheat | 6 | 7 | 8 | 9 | 8 | 8 | 9 | 9 |
| Avena fatua country: Morocco | 2 | 4 | 4 | 6 | 3 | 8 | 9 | 9 |
| wheat | 7 | 8 | 8 | 9 | 7 | 8 | 9 | 9 |
| Avena fatua country: Italy | 3 | 3 | 5 | 8 | 2 | 2 | 9 | 9 |
| wheat | 7 | 8 | 9 | 9 | 8 | 8 | 9 | 9 |
| Avena fatua country: USA | 4 | 4 | 8 | 8 | 9 | 9 | 9 | 9 |
| wheat | 8 | 8 | 8 | 9 | 8 | 8 | 9 | 9 |
| Avena fatua | 2 | 2 | 2 | 2 | 3 | 8 | 9 | 9 |

TEST B

Growth inhibition of grasses (post emergence method)

Seeds of the grasses Lolium perenne, Poa pratensis, Festuca ovina and Dactylis glomerata were sown in plastic dishes filled with an earth/turf/sand mixture and watered normally. Each week the emergent grasses were cut back to a height of 4 cm above the soil and then sprayed with aqueous spray broths of the active substances of the formula I 40 days after sowing and 1 day after the last cutting. The amount of active substance corresponded to a rate of application of 5 kg per hectare. The growth of the grasses was evaluated 10 and 21 days after application using the following linear scale rating:

1 = pronounced inhibition (no further growth from the time of application)
9 = no inhibition (growth as untreated control)

The results are given in the table below.

| Compound No. application | 1 | 2 | 3 | 6 | 26 | 42 |
|---|---|---|---|---|---|---|
| rate in kg/ha | 5 | 5 | 5 | 5 | 5 | 5 |
| Lolium perenne | 7 | 8 | 8 | 5 | 6 | 8 |
| Poa pratensis | 5 | 5 | 6 | 3 | 3 | 7 |
| Festuca | 4 | 4 | 5 | 3 | 3 | 6 |
| Dactylis glomerata | 3 | 6 | 4 | 2 | 3 | 5 |

GROWTH INHIBITION IN CEREALS

In the same manner as with grasses, the growth inhibition of different crop-cereals was tested in the greenhouse. The test was run exactly in the same manner as with the grasses. The results are given in the table below.

| Compound No. application | 1 | | 3 | | 6 | | 26 | | 41 | | 42 | | 44 | | 54 | |
|---|---|---|---|---|---|---|---|---|---|---|---|---|---|---|---|---|
| rate in kg/ha | 6 | 2 | 6 | 2 | 6 | 2 | 2 | 6 | 6 | 2 | 6 | 2 | 6 | 2 | 6 | 2 |
| wheat | 5 | 6 | 6 | 7 | 4 | 5 | 5 | 8 | 6 | 8 | 4 | 6 | 4 | 5 | 7 | 8 |
| rye | — | — | — | — | 4 | 5 | — | — | — | — | 6 | 7 | 6 | 7 | — | — |
| barley | 6 | 7 | 3 | 7 | 5 | 6 | 3 | 8 | 5 | 7 | 6 | 7 | 5 | 7 | 5 | 7 |
| rice | 6 | 0 | — | — | 8 | 9 | — | — | 5 | 6 | 7 | 7 | 9 | 9 | 7 | 9 |

TEST C

Growth Inhibition in Soya Beans

Soja plants of the variety "Hark" were grown from earthenware pots in a green house under controlled, optimal conditions for their growth. Three week after they had emerged, the young plants were sprayed until dripoff with a test-liquor, containing one of the compounds to be tested in the indicated concentrations of respectively 100 and 500 ppm. Some of the plants were left untreated to serve as control.

The test was assessed four weeks after this treatment. The height of the plant was measured and evaluated according to the following scale:

| | |
|---|---|
| 1 | strong inhibition, no further growth after application. Medium height of plant about 18 cm. |
| 2-8 | intermediate stages of inhibition. |
| 9 | no inhibition, plant growth like untreated control plant. Medium height about 40 cm. |

The results are summarized in the table below.

| Compound No. application conc. | growth inhibition | |
|---|---|---|
| | 500 ppm | 100 ppm |
| 1 | 2 | 3 |
| 2 | 4 | 6 |
| 3 | 2 | 6 |
| 6 | 2 | 4 |
| 14 | 1 | 8 |
| 26 | 3 | 9 |
| 41 | 2 | 4 |
| 42 | 1 | 9 |
| 44 | 3 | 9 |
| 45 | 3 | 7 |
| 54 | 3 | 9 |

TEST D

Inhibition of the Growth of Side Shoots (Suckers) in Tobacco-Plants

In the green-house tobacco plants of the variety "Nicotina" were grown. 10 weeks after seeding, shortly before flowering, the main shoot (stem) was cut off. The day after, groups of three plants were sprayed from above with 10 ml of an aqueous emulsion of the test-compound. The concentrations chosen corresponded to 12, 6, 3 and 1.5 kg per hectare. Two weeks after this treatment, the inhibitory action on the topmost six shoots was evaluated. The length of the sucker-shoot i.e. the shoots, that had grown after cutting off the main shoot was measured and compared to those of groups of untreated control plants. As comparison "Off-Shoot T ®", a commercially used product for this purpose was used.

The results were evaluated as follows:

| | |
|---|---|
| 9 | normal sucker growth (100%) as in untreated control plants |
| 8-2 | percentually reduced growth of suckers |
| 1 | no growth after treatment (no suckers developed) |

The results are given in the table below

| Compound tested | application rate in kg/ha | result |
|---|---|---|
| 1 | 6 | 2 |
| | 3 | 2 |
| | 1.5 | 2 |
| 2 | 6 | 2 |
| | 3 | 2 |
| | 1.5 | 3 |
| 4 | 6 | 2 |
| | 3 | 2 |
| | 1.5 | 3 |
| 42 | 6 | 2 |
| | 3 | 2 |
| | 1.5 | 2 |
| 47 | 6 | 2 |
| | 3 | 2 |
| | 1.5 | 3 |
| 63 | 6 | 2 |
| | 3 | 2 |
| | 1.5 | 2 |
| 76 | 6 | 2 |
| | 3 | 2 |
| | 1.5 | 2 |
| mixture C9 and C10 alkanols | 12 | 4 |
| | 6 | 7 |
| | 3 | 9 |

We claim:

1. An ester of 1,2-diphenyl-cyclohex-1-ene-4-carboxylic acid of the formula

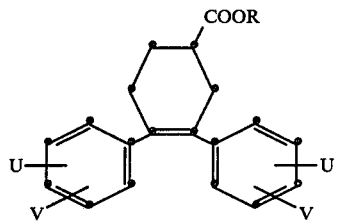

wherein

R is $C_1$–$C_7$ alkyl optionally substituted by halogen, nitro, $C_1$–$C_4$ alkoxy, $C_3$–$C_8$ cycloalkyl, by phenyl or phenoxy unsubstituted or substituted by chlorine, bromine, $C_1$–$C_4$ alkyl or $C_1$–$C_4$ alkoxy; $C_3$–$C_7$ alkenyl optionally substituted by chlorine or $C_1$–$C_4$ alkyl; $C_3$–$C_7$ alkynyl; $C_3$–$C_6$ cycloalkyl optionally substituted by chlorine; phenyl or benzyl unsubstituted or substituted by chlorine, bromine, $C_1$–$C_4$ alkyl, $C_1$–$C_4$ alkoxy, nitro, amino, mono- or di($C_1$–$C_4$)alkylamino or trifluoromethyl and U and V are each selected from the group consisting of hydrogen, chlorine, bromine, $C_1$–$C_4$ alkyl, $C_1$–$C_4$ alkoxy, nitro and trifluoromethyl, with the proviso that if all U's and V's are hydrogen, R is not unsubstituted alkyl.

2. An ester according to claim 1 wherein R is $C_1$–$C_7$ alkyl substituted by halogen, nitro, $C_1$–$C_4$ alkoxy, $C_3$–$C_8$ cycloalkyl or by phenyl or phenoxy unsubstituted or substituted by chlorine, bromine, $C_1$–$C_4$ alkyl or $C_1$–$C_4$ alkoxy.

3. The ester according to claim 2 which is 1,2-diphenyl-cyclohex-1-ene-4-carboxylic acid 3'-nitrobut-2'-yl ester.

4. The ester according to claim 2 which is 1,2-diphenyl-cyclohex-1-ene-4-carboxylic acid 2'-chloroethyl ester.

5. An ester according to claim 1 wherein R is $C_3$–$C_7$ alkenyl optionally substituted by chlorine or $C_1$–$C_4$ alkyl; or $C_3$–$C_7$ alkynyl.

6. The ester according to claim 5 which is 1,2-diphenyl-cyclohex-1-ene-4-carboxylic acid 4'-pentenyl ester.

7. The ester according to claim 5 which is 1,2-diphenyl-cyclohex-1-ene-4-carboxylic acid 2'-propynyl ester.

8. An ester according to claim 1 wherein R is phenyl or benzyl unsubstituted or substituted by chlorine, bromine, $C_1$–$C_4$ alkyl, $C_1$–$C_4$-alkoxy, nitro, amino, mono- or di-($C_1$–$C_4$ alkyl)amino or trifluoromethyl.

9. The ester according to claim 8 which is 1,2-diphenyl-cyclohex-1-ene-4-carboxylic acid 4'-chlorobenzyl ester.

10. The ester according to claim 8 which is 1,2-diphenyl-cyclohex-1-ene-4-carboxylic acid 3'-N,N-dimethylaminophenyl ester.

11. An ester according to claim 1 wherein at least one of U and V is selected from the group consisting of chlorine, bromine, $C_1$–$C_4$ alkyl, $C_1$–$C_4$ alkoxy, nitro and trifluoromethyl.

* * * * *